US009510881B2

(12) United States Patent
Castaneda et al.

(10) Patent No.: US 9,510,881 B2
(45) Date of Patent: Dec. 6, 2016

(54) METHOD OF STABILIZING A FRACTURE AT A METAPHYSIS DEFINING A CONCAVE ARTICULAR SURFACE (71) Applicant: BIOMET C.V., Gibraltar (GI)

(72) Inventors: Alfredo Castaneda, Miami, FL (US); Eduardo A. Ampuero, Miami, FL (US)

(73) Assignee: Biomet C.V., Gibraltar (GI)

( * ) Notice: Subject to any disclaimer, the term of this patent is extended or adjusted under 35 U.S.C. 154(b) by 193 days.

(21) Appl. No.: 14/291,113

(22) Filed: May 30, 2014

(65) Prior Publication Data
US 2014/0330321 A1  Nov. 6, 2014

Related U.S. Application Data (63) Continuation of application No. 13/364,513, filed on Feb. 2, 2012, now Pat. No. 8,790,378.

(51) Int. Cl.
*A61B 17/80* (2006.01)
*A61B 17/56* (2006.01)

(52) U.S. Cl.
CPC ...... *A61B 17/8061* (2013.01); *A61B 2017/564* (2013.01)

(58) Field of Classification Search
CPC .................. A61B 17/8061; A61B 17/8085
See application file for complete search history.

(56) References Cited

U.S. PATENT DOCUMENTS

| 3,741,205 A | 6/1973 | Markolf et al. |
| 3,842,825 A | 10/1974 | Wagner |
| 4,219,015 A | 8/1980 | Steinemann |
| 4,388,921 A | 6/1983 | Sutter et al. |
| 4,573,458 A | 3/1986 | Lower |

(Continued)

FOREIGN PATENT DOCUMENTS

| DE | 8628766 | 12/1986 |
| EP | 0206767 | 12/1986 |

(Continued)

OTHER PUBLICATIONS 2.4 mm Variable Angle LCP Distal Radius System. For fragment-specific fracture fixation with variable angle locking technology. Technique Guide, Synthes, 2008.

(Continued)

*Primary Examiner* — David Bates
*Assistant Examiner* — Olivia C Chang
(74) *Attorney, Agent, or Firm* — Schwegman Lundberg & Woessner, P.A.

(57) ABSTRACT

A volar distal radius plate includes a shaft and a head. The head includes a radial side that seats below the volar rim, and an ulnar side with two extending tabs that provide a buttress support to ulnar fragments from the volar rim. The tabs are contoured to be atraumatic to the overlying soft tissue. The tabs can be readily re-orientated to better approximate the volar rim and provide close support to the volar fragments. Each tab includes a single hole specifically sized to closely receive a K-wire in a fixed angle orientation, and which permits the K-wire to apply a bending load to a tab in situ to bend the tab about a lower recess between the tab and the remainder of the head. Therefore, the plate does not require a dedicated bender. The tabs can also accommodate sutures.

20 Claims, 3 Drawing Sheets

(56) References Cited

U.S. PATENT DOCUMENTS

| | | |
|---|---|---|
| 4,955,886 A | 9/1990 | Pawluk |
| 4,973,332 A | 11/1990 | Kummer |
| 5,057,109 A | 10/1991 | Olerud |
| 5,147,361 A | 9/1992 | Ojima et al. |
| 5,616,144 A | 4/1997 | Yapp et al. |
| 5,647,712 A | 7/1997 | Demirdogen et al. |
| 5,772,662 A | 6/1998 | Chapman et al. |
| 5,954,722 A | 9/1999 | Bono |
| 6,004,353 A | 12/1999 | Masini |
| 6,123,709 A | 9/2000 | Jones |
| 6,206,881 B1 | 3/2001 | Frigg et al. |
| 6,364,882 B1 | 4/2002 | Orbay |
| 6,454,769 B2 | 9/2002 | Wagner et al. |
| 6,506,191 B1 | 1/2003 | Joos |
| 6,565,570 B2 | 5/2003 | Sterett et al. |
| 6,623,486 B1 | 9/2003 | Weaver et al. |
| 6,652,530 B2 | 11/2003 | Ip et al. |
| 6,712,820 B2 | 3/2004 | Orbay |
| 6,786,909 B1 | 9/2004 | Dransfeld et al. |
| 6,866,665 B2 | 3/2005 | Orbay |
| 7,189,237 B2 | 3/2007 | Huebner |
| 7,250,053 B2 | 7/2007 | Orbay |
| 7,294,130 B2 | 11/2007 | Orbay |
| 7,335,204 B2 | 2/2008 | Tornier |
| 7,604,657 B2 | 10/2009 | Orbay et al. |
| 7,818,542 B2 | 10/2010 | Shen et al. |
| 7,935,126 B2 | 5/2011 | Orbay et al. |
| 7,951,176 B2 | 5/2011 | Grady, Jr. et al. |
| 8,021,402 B2 | 9/2011 | Martin et al. |
| 8,469,999 B2 | 6/2013 | Gonzalez-Hernandez |
| 8,632,574 B2 | 1/2014 | Kortenbach et al. |
| 8,790,378 B2 | 7/2014 | Castaneda et al. |
| 2004/0210220 A1* | 10/2004 | Tornier .............. A61B 17/8061 606/284 |
| 2005/0085818 A1 | 4/2005 | Huebner |
| 2005/0234458 A1 | 10/2005 | Huebner |
| 2007/0093837 A1 | 4/2007 | Bohrmann et al. |
| 2007/0233111 A1 | 10/2007 | Orbay |
| 2008/0140127 A1 | 6/2008 | Vasta et al. |
| 2009/0018587 A1 | 1/2009 | Bottlang |
| 2009/0143825 A1 | 6/2009 | Graham |
| 2009/0275987 A1 | 11/2009 | Graham et al. |
| 2010/0057086 A1 | 3/2010 | Price et al. |
| 2011/0118795 A1 | 5/2011 | Hashmi et al. |
| 2013/0079828 A1* | 3/2013 | Glickel .............. A61B 17/8061 606/281 |

FOREIGN PATENT DOCUMENTS

| | | |
|---|---|---|
| FR | 742618 | 3/1933 |
| GB | 2477086 | 7/2011 |
| WO | WO 89/04150 | 5/1989 |
| WO | WO 97/09000 | 3/1997 |
| WO | WO 01/30251 | 5/2001 |
| WO | WO-2013115911 A1 | 8/2013 |

OTHER PUBLICATIONS

"U.S. Appl. No. 13/364,513, Non Final Office Action mailed Sep. 11, 2013", 8 pgs.

"U.S. Appl. No. 13/364,513, Non Final Office Action mailed Dec. 9, 2013", 9 pgs.

"U.S. Appl. No. 13/364,513, Notice of Allowance mailed Mar. 28, 2014", 5 pgs.

"U.S. Appl. No. 13/364,513, Response filed Feb. 28, 2014 to Non Final Office Action mailed Dec. 9, 2013", 20 pgs.

"U.S. Appl. No. 13/364,513, Response filed Oct. 9, 2013 to Non Final Office Action mailed Sep. 11, 2013", 17 pgs.

"European Application Serial No. 12816809.3, Communication pursuant to Article 94(3) EPC mailed Aug. 25, 2015", 6 pgs.

"European Application Serial No. 12816809.3, Office Action mailed Sep. 11, 2014", 2 pgs.

"European Application Serial No. 12816809.3, Response filed Mar. 5, 2015 to Office Action mailed Sep. 11, 2014", 13 pgs.

"International Application Serial No. PCT/US2012/069342, International Preliminary Report on Patentability mailed Aug. 14, 2014", 8 pgs.

"International Application Serial No. PCT/US2012/069342, International Search Report mailed Feb. 22, 2013", 4 pgs.

"International Application Serial No. PCT/US2012/069342, Written Opinion mailed Feb. 22, 2013", 6 pgs.

* cited by examiner

METHOD OF STABILIZING A FRACTURE AT A METAPHYSIS DEFINING A CONCAVE ARTICULAR SURFACE

CROSS-REFERENCE TO RELATED APPLICATION

This application is a continuation of U.S. Ser. No. 13/364,513, filed Feb. 2, 2012, which is hereby incorporated by reference herein in its entirety.

BACKGROUND OF THE INVENTION

1. Field of the Invention

This invention relates broadly to surgical implants. More particularly, this invention relates to a bone fracture fixation system for distal radius fractures.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate typically placed against the side of a bone, and screws extending from the plate into holes drilled in the bone fragments to provide stabilized fixation of the fragments. However, many currently available plate systems fail to provide desirable alignment and stabilization.

The distal radius exhibits a concave shape extending from the shaft, which reaches an inflection point at a so-called watershed line followed by a convex like form at its most prominent feature, the volar rim. With a distal radius fracture, the complex shape of the distal radius, including the prominent volar rim of the lunate fossa, relatively flat volar rim of the scaphoid fossa, and the sometimes prominent base of the styloid process should be accommodated. Furthermore, the ligaments extending from the volar side of the distal radius to the intercarpal bones must not be irritated or distressed. Moreover, a fixation device should provide desirable alignment and stabilization of the bone structure proximate the articular surface of the distal radius.

Co-owned U.S. Pat. No. 7,250,053 to Orbay discloses a volar plate for the distal radius that accommodates the anatomy. The plate includes a head for placement at the metaphysis and a shaft for extension along the diaphysis. The head and shaft each include holes for receiving fasteners to couple the plate to the bone. The holes in the head are threaded fixed angle holes oriented to extend the shaft of the fasteners in a spatial distribution through the bone about the articular surface to provide significant support and early mobility. In addition, the top portions of the plate are such that they provide a buttress support for the fragment while providing a smooth contour to minimize soft tissue interaction and not creating a prominent sharp edge nearest the inflexion point or 'watershed line' of the volar rim. This is achieved by a contoured shape that blends back into the anatomy without extending into the articular surface. The lower surface of the ulnar side of the head of this plate is contoured to accommodate the concave shape of the distal radius below the watershed line. It is specifically indicated that the watershed line is not to be violated by the plate.

However, volar ulnar facet fractures occur in the distal portion of the concave form of the distal radius and require additional fixation. The fractures may involve displaced avulsions, shear fractures and small fragments that are in the vicinity of the prominent portion of the volar rim. These fractures are difficult to treat with existing hardware since most available hardware could interfere with surrounding soft tissue and/or increase the likelihood impinging on the articular surfaces of the distal radius.

US Pub. No. 2009/0275987 to Graham proposes various plates and adjunct extenders that can be physically attached to the plates with screws to provide supplementary anatomical support. The extenders are not ideally shaped to limit interference with soft tissue. In addition, this type of support requires the attachment of very small plates to the primary plate and can be difficult to work with, particularly in the operating room and during a surgical procedure. There is no easy and reliable way to fit the extenders to the anatomy during the procedure.

SUMMARY OF THE INVENTION

A volar distal radius plate is provided having a shaft for placement on the diaphysis of the distal radius bone, and a head angled relative to the shaft and shaped for low profile placement on the metaphysis of the distal radius bone. The plate has a lower bone contacting surface and an opposite upper surface.

The head of the plate is shaped to primarily seat below the boney crest inflexion point of the 'watershed line' at the distal radius. The head and shaft each include holes for receiving fasteners to couple the plate to the bone. The holes in the head are threaded, fixed angle holes, arranged in two rows. The holes are oriented to extend screws in a spatial distribution through the bone and about the articular surface of the wrist socket to provide significant support. The threaded fixed angle holes are provided within the head to be located below the boney crest or watershed line of the distal radius.

The radial side of the plate seats completely below the watershed line. The ulnar (or medial) side of the plate is provided with two smoothly contoured and chamfered distally extending tabs for extension over and beyond the watershed line when the plate is positioned on the bone. The tabs provide a buttress support over the volar ulnar facet.

The tabs each have a smoothly contoured upper surface that is adapted to be atraumatic to the soft tissue and thereby minimize soft tissue irritation. In addition, the tabs can be readily re-orientated to approximate the volar rim and provide close support. In order to re-orient the tabs, the tabs are provided with respective lower recesses, preferably as an undercut at the junction of the tabs and the remainder of the head plate; i.e., in a preferred embodiment, from the lower surface of the plate, the undercut and distal edge of the lateral side of the plate are in alignment. The recesses allow each tab to be contoured independently to fit the patient anatomy. Each tab is provided with a single hole specifically sized to closely receive a K-wire in a fixed angle orientation. This permits a K-wire to apply a bending load to a tab in situ to bend the tab about its lower recess into a new orientation to best match the patient anatomy and provide support. Therefore, the plate does not require a dedicated bender. In addition, the hole in each tab is spaced relative to the distal peripheral edge of the tab to accommodate passage of a suture needle completely therethrough.

DETAILED DESCRIPTION OF THE PREFERRED EMBODIMENTS

Turning now to FIGS. 1 through 4, a bone plate 10 for stabilization of a fracture of a distal radius bone 100 is shown. The plate 10 includes a shaft 12 for placement on the diaphysis 102 of the distal radius bone 100, and a head 14 at a transverse orientation relative to the shaft for placement on the metaphysis 104. The plate includes a bone contacting lower surface 16 and an opposite upper surface 18. The head is in angled upward relative to the shaft when the lower surface 16 of the shaft is positioned substantially horizontal and face down in contact with the diaphysis of the radius bone.

The shaft 12 and head 14 each include holes for receiving fasteners to couple the plate 10 to the bone 100. The shaft 12 preferably includes a combination of compression holes 20, 22 and non-compression fixed angle, threaded holes 24. The compression holes preferably comprise both circular holes 20 and elongate slots 22. Preferably, the holes 20, 22, 24 comprise the system of holes described in co-owned and co-pending U.S. Ser. No. 13/313,350, filed Dec. 7, 2011, which is hereby incorporated by reference herein in its entirety. Holes of another design for suitable fasteners may also be used; however, it is preferable that any provided holes and arrangement thereof include both circular holes and slots, and that such circular holes include a combination of compression holes for compression fasteners and fixed angled holes such as can accommodate a fastener with a threaded head in a fixed orientation. The plate may also include one of more K-wire holes 26 to closely receive respective K-wires for temporary fixation of the shaft 12 of the plate relative to the bone 100.

The holes 28 in the head of the plate 14 are threaded, fixed angle holes, with the threads of each hole defining a respective fixed axis for a fastener inserted therethrough. In a preferred embodiment, the threaded holes 28 are preferably of a same configuration and size as the threaded holes 24, and thus capable of receiving and fixing a common fastener therewith. One exemplar fastener 150 is shown in phantom in FIG. 2. The holes 28 are preferably arranged in two rows; a relatively proximal row 30 and a relatively distal row 32, the rows 30, 32 being acutely angled relative to each other. In a preferred embodiment, the proximal row 30 of holes includes four threaded holes 28, and the distal row 32 includes three threaded holes 28 preferably arranged in an offset from the proximal row 30 such that the shafts of fasteners inserted in the proximal row 30 can extend distally between the shafts of the fasteners inserted in the distal row 32 in an interleaved manner. More preferably, when the plate is positioned on the bone at the intended location, the fasteners 150 extend into the bone in a spatial distribution about the articular surface 106 (FIG. 4) of the wrist socket to provide subchondral support. All the threaded fixed angle holes 28 within the head 14 of the plate are provided to be located in the subchondral bone below the inflexion point of the watershed line (seen also in FIG. 6) on the volar side of the distal radius. Preferred locations of the threaded holes 28 relative to the volar distal radius and preferred axial orientations of such threaded holes are described in detail in U.S. Pat. No. 7,294,130, which is hereby incorporated by reference herein in its entirety.

K-wire holes are also preferably provided relative to the threaded holes in the head of the plate. Two K-wire holes 34, 36 are provided between respective sets of adjacent holes in the proximal row 30 of threaded holes. The K-wire holes 34, 36 are sized to closely receive a K-wire such that an appropriately sized K-wire inserted therethrough is retained at a fixed angle relative to the plate 10 by the sidewalls of the respective K-wire hole. Such holes can be used for temporary fixation of the plate to the bone. Further, the K-wire, whether or not providing such temporary fixation, can be examined under fluoroscopy to analyze its trajectory relative to the bone anatomy and thereby provide information with respect to the apparent trajectory of fasteners through the adjacent threaded holes. In this manner, the K-wires inserted through the K-wire holes provided feedback as to the appropriate placement of the plate prior to drilling larger holes in the bone for the relatively larger fasteners. An additional K-wire hole 38 is preferably provided between two of the holes in the distal row 32. In addition, other small holes, such as 38 can be provided to the head of the plate. Such other small holes may be additional K-wire holes of the types described for the purpose of guiding a K-wire or the plate relative to the K-wire, or may be of the same or different structure so as to be otherwise adapted as anchor holes for suture to secure bone fragments and soft tissue relative to the plate.

Figure 1:
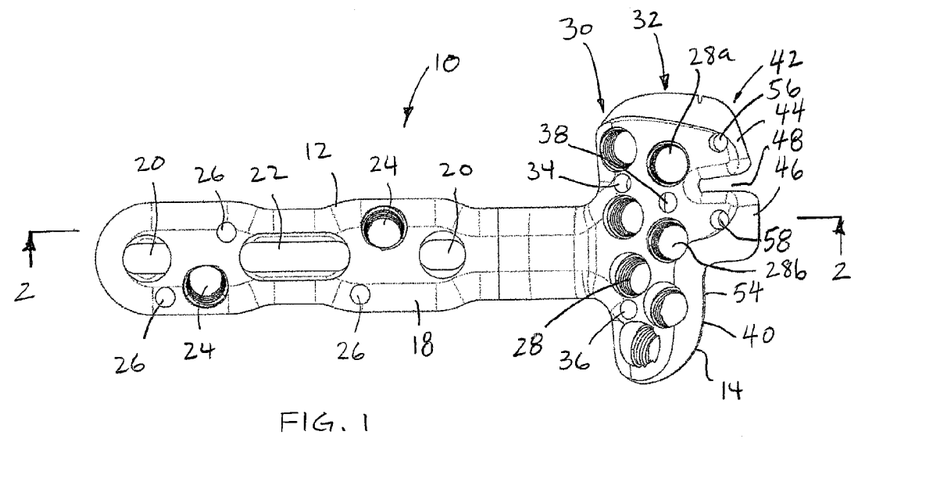
FIG. 1 is a top view of a distal radius plate according to the invention.
Figure 2:
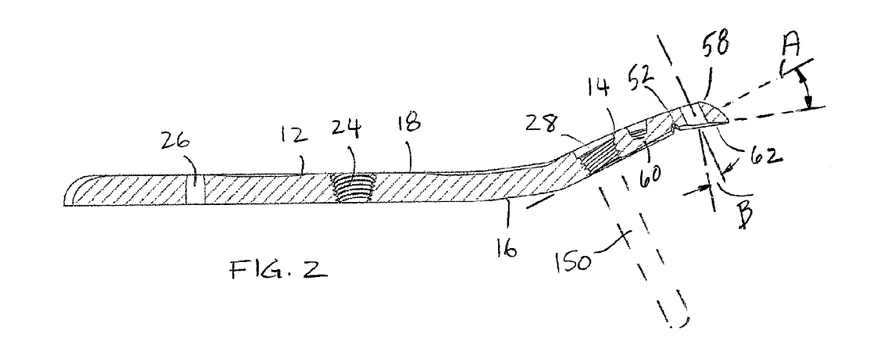
FIG. 2 is a longitudinal section view along line 2-2 in FIG. 1.
Figure 3:
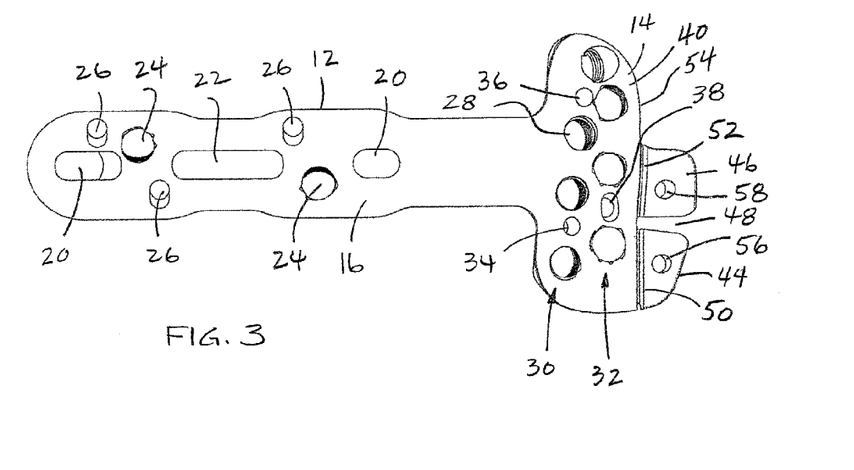
FIG. 3 is a bottom view of the plate of FIG. 1.
Figure 4:
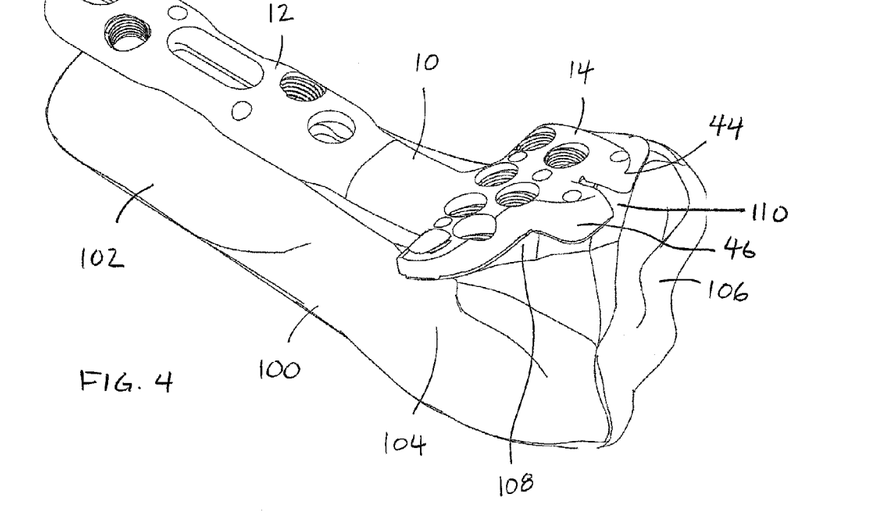
FIG. 4 is a perspective view of the plate of FIG. 1 shown on a portion of a distal radius bone.
Figure 5:
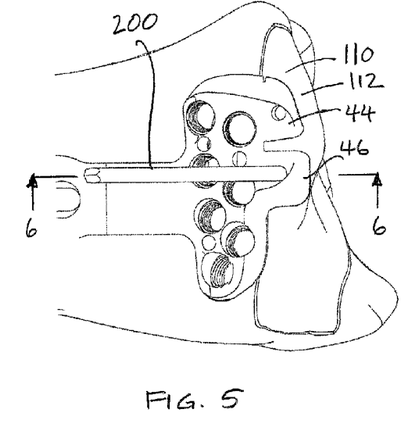
FIG. 5 is a top view and a FIG. 6 is a longitudinal section view along line 6-6 in FIG. 5, both illustrating insertion of a K-wire into a hole in an extension tab of the distal radius plate prior to bending of the tab.

Referring to FIGS. 1 and 3, the radial side 40 of the plate 10 is tapered to a distal edge 54 and sized and shaped to seat completely below the 'watershed' inflexion line 108 of the boney crest. In distinction, the ulnar (i.e., medial) side 42 of the distal edge of the plate is provided with two distally extending tabs 44, 46 separated from each other by a space 48. While the tabs 44, 46 extend from the ulnar (i.e., medial) side 42 of the distal edge, the tabs do not extend the lateral dimension of the head of the plate; the entire extension is preferably distal and displaced to the ulnar side. The tabs 44, 46 extend approximately 5 mm beyond the distal end 54 of the plate such that the tabs 44, 46 extend beyond the 'watershed' inflexion line of the distal radius bone when the plate is properly positioned on the bone in order to provide a support to the volar fragment, and particularly the ulnar facet 110 thereof (FIGS. 4 and 5). This allows the tabs 44, 46 to claw or buttress the volar fragment. In a preferred embodiment, the tabs 44, 46 may be considered to be located as an ulnar side tab 44 and an intermediate tab 46, with 'intermediate' defining a location between the ulnar and radial sides of the distal radius when the plate is positioned on the volar side of the distal radius (and not a relative location between other tabs). The ulnar side tab 44 is located distally in front of the medialmost (ulnar side) threaded hole 28a of the distal row 32 of threaded holes 28, and the intermediate tab 46 is located distally in front of the central threaded hole 28b of the distal row 32 of threaded holes 28 (FIG. 1). The tabs 44, 46 each have a smoothly contoured and chamfered upper surface which tapers toward the medial side of the relatively ulnar side tab 44 and toward the lateral side of the intermediate tab 46. This provides the upper surface of the tabs 44, 46 with an atraumatic soft tissue contacting surface that minimizes soft tissue irritation. Referring specifically to FIG. 2, the lower surfaces 62 of the tabs are angled relative to the lower surface 60 at the remainder of the lower surface of the head 14. That is, while the remainder of the lower surface 60 of the head 14 is configured to seat in the concavity on the bone below the 'watershed' inflexion line of the distal radius, the tabs 44, 46 are configured to extend over the watershed line and generally parallel to the volar rim 110. Thus, the lower surfaces 62 of the tabs 44, 46 extend out of orientation with the lower surface 60 of the remainder of the head by an acute angle shown at A. Angle A is preferably between 26° and 30°.

Figure 6:
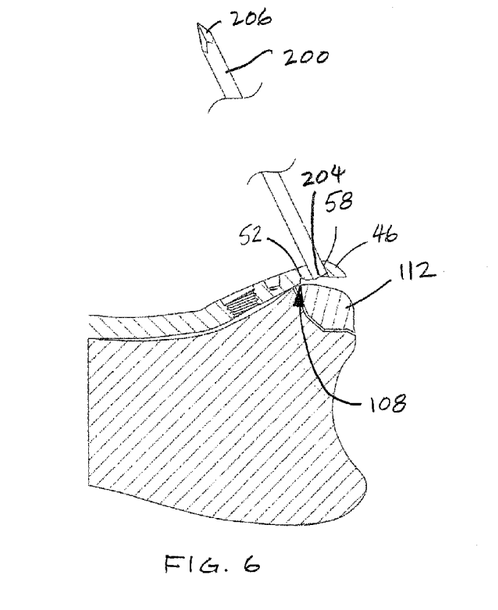
Figure 7:
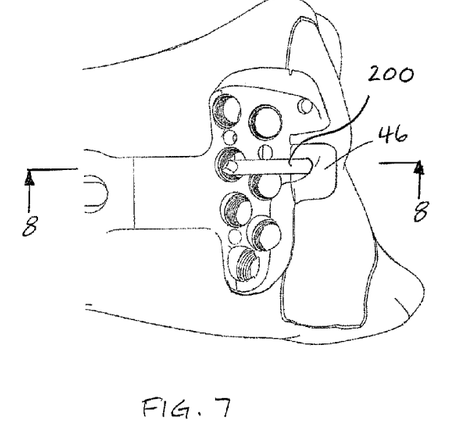
FIG. 7 is a top view and a FIG. 8 is a longitudinal section view along line 8-8 in FIG. 7, both illustrating use of a K-wire for bending of the extension tab of the distal radius plate with the K-wire inserted into the hole in the extension tab.
Figure 8:
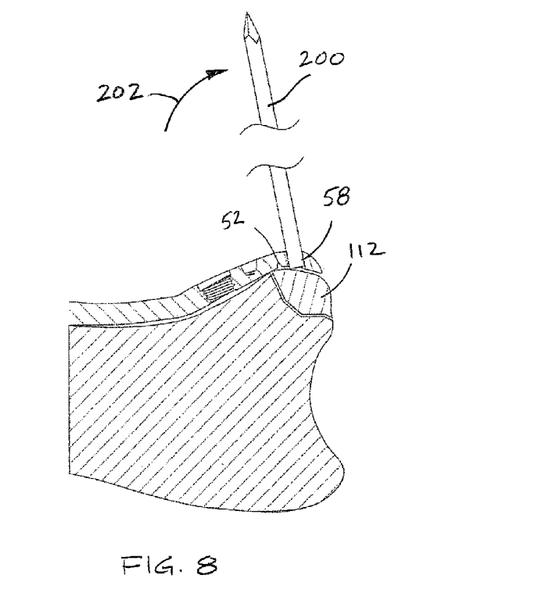

Referring to FIGS. 2 and 3, in accord with the invention, the tabs 44, 46 can be readily re-orientated in situ to better approximate the volar rim 110 and provide close support to a fragment of the volar rim. Each tab 44, 46 is provided with a single K-wire hole 56, 58 each defined by a cylindrical sidewall and specifically sized to closely receive a 1.6 mm K-wire in a fixed angle orientation. A fixed angle orientation is one in which the K-wire is retained coaxial with or within 5°, and more preferably within 3°, of the axis of the K-wire hole. With too much play between the K-wire and plate, the K-wire cannot positively engage the hole to provide accurate bending of the tabs in accord with the desired operation of the system. With respect to K-wire hole 58, the hole has an approximate diameter of 1.6 mm to provide the necessary clearance for passage of the K-wire. The axes of the holes 56, 58 in the tabs 44, 46 are oblique relative to the lower surface 16 at the tabs, as shown by angle β (FIG. 2) and also seen in FIG. 3. The tabs 44, 46 are provided with respective lower recesses 50, 52 preferably formed as an undercut at the junction of the tabs and the remainder of the head of the plate; i.e., in a preferred embodiment, from the lower surface 16 of the plate, the recesses 50, 52 and distal edge 54 of the radial side 40 of the plate are in alignment. The recesses 50, 52 reduce the cross-sectional area moment of inertia at the junction between the tabs 44, 46 and the remainder of the head 14 without requiring that the width of the tabs be reduced. That is, it is preferable that the junctions between the tabs and the remainder of the head are not reduced in the width (in a medial-lateral direction) relative to the respective tabs. As a result of the reduced cross-sectional area moment of inertia at the junctions, when a force is applied to a tab, all plastic deformation will be located at the reduced cross-sectional area—leaving the tab and the K-wire hole without deformation—and the tabs 44, 46 will be re-oriented about an axis in alignment with the radial side distal edge 54. The recesses 50, 52 allow each tab 44, 46 to be contoured independently of the other to fit the patient anatomy. Referring to FIGS. 5-8, with the K-wire 200 inserted into the K-wire hole 58 of tab 46, the K-wire 200 is able to apply a bending load to the tab 46 in situ to bend the tab about its lower recess 52, e.g., in the direction of arrow 202, into a new orientation to best match the patient anatomy and provide support for the ulnar facet of the volar rim 110. Therefore, the plate does not require a dedicated bender. Moreover, the K-wire 200 is an extremely unobtrusive tool for use during the surgical procedure, providing excellent visibility to the remainder of the plate 10 and surgical wound during the bending operation to allow the surgeon to visually confirm plate-to-anatomy conformation. Using the K-wire 200, the tabs 44, 46 can be bent independently, quickly, and accurately to fit the anatomy. Referring to FIG. 6, it is preferable that, for purposes of tab bending, a K-wire 200 be inserted blunt side 204 down toward the bone to prevent the sharpened tips 206 at the opposite end from catching the bone and inhibiting bending or inadvertently displacing loose bone fragments.

In addition, the K-wire holes 56, 58 can be used for stable, temporary fixation of a volar rim fragment relative to the plate 10 and the remainder of the distal radius 100 with a K-wire. In such use, one or more K-wires are preferably inserted via a drill, with the sharpened side 206 of the K-wire inserted down into the bone.

Figure 9:
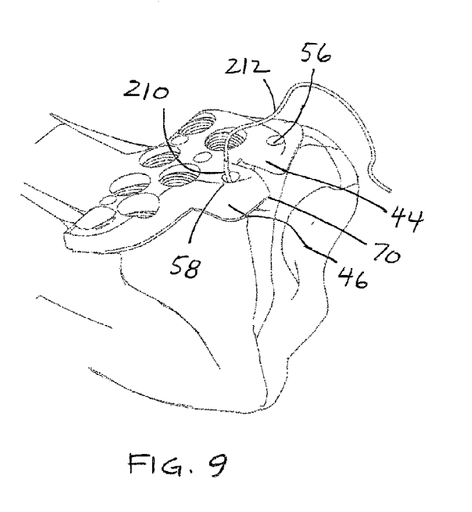
FIGS. 9 and 10 are perspective views illustrating the advancement of a suture needle and suture through the hole in an extension tab to secure soft tissue at the joint capsule.
Figure 10:
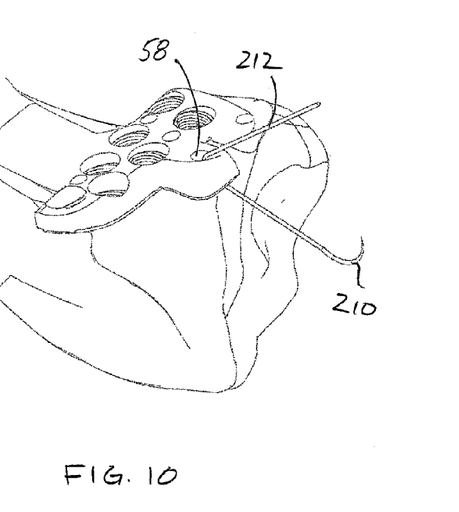

Turning now to FIGS. 9 and 10, the tabs 44, 46 and K-wire hole 56, 58 in each tab is spaced relative to the distal peripheral edge 70 of the respective tab to accommodate passage of a ⅜ inch circle suture needle 210 completely therethrough. For this purpose and other reasons, the holes 56, 58 are each displaced preferably approximately 2.5 mm from the edge 70 of the respective tabs 44, 46. In addition, the tabs each have a maximum thickness of 2.0 mm. In view of this structure, and by way of example, a ⅜ inch circle ETHICON P3 suture needle can be passed completely through the hole 58 in tab 46. This allows the tab 46 to receive suture 212 to capture the smallest bone fragment and further repair the joint capsule at the fracture site.

The plate provides stability to volar distal radius fractures, particularly where support of the volar rim is desirable. The tabs extending from the ulnar side of the plate do not require any attachment to the plate at the time of the surgical procedure; they are integrated into the plate preventing the potential for otherwise loose components to drop into the surgical wound, reduce implantation time, and eliminate potential difficulties. Further, the tabs are easily bent to confirm to the underlying boney anatomy to best buttress the volar rim and/or place suture holes in a location suitable for soft tissue repair. Also, such tabs are designed to be non-irritating to surrounding soft tissue.

There have been described and illustrated herein embodiments of a volar distal plate. While particular embodiments of the invention have been described, it is not intended that the invention be limited thereto, as it is intended that the invention be as broad in scope as the art will allow and that the specification be read likewise. That is, while an embodiment with a specified number of threaded holes in the plate is described, it is appreciated that a greater or fewer number of threaded holes can be provided in the head of the plate. By way of example, the distal row of threaded holes can include at most two threaded holes. In addition, while the plate is described as having two tabs, it will be appreciated that another number of tabs may be provided to the plate. For example, a single tab may be provided to the ulnar side of the head of the plate. It will therefore be appreciated by those skilled in the art that yet other modifications could be made to the provided invention without deviating from its spirit and scope as claimed.

What is claimed is:

1. A method of stabilizing a fracture of a bone, the bone having a diaphyseal portion and a metaphyseal portion and having a concave articular surface at the end of the metaphyseal portion and a rim extending at least partially about the articular surface, the method comprising:
    a) providing a bone plate having a bone contacting surface, an opposite surface, a shaft portion defining a longitudinal axis and including a plurality of fastener holes to secure the shaft portion relative to the diaphyseal portion of the bone, and a head portion angled relative to the shaft portion to secure the head portion relative to the metaphyseal portion of the bone, the head portion having a first side and an opposing second side and a plurality of fastener holes provided therein adapted to receive fasteners therethrough, the first side of the head portion tapering to a distal edge and being free and absent of any tab, the second side of the head portion provided with a reorientable tab unitary with the head portion which extends longitudinally beyond the distal edge of the first side of the head portion, a recess provided between the tab and a junction with the head portion in alignment with the distal edge of the first side;
    b) positioning the plate on the bone such that first side of the head portion seats proximally below the rim of the metaphyseal portion, and the tab extends over the rim of the metaphyseal portion, the recess reducing a cross-sectional area moment of inertia at the junction; and
    c) reorienting the tab to contour to the rim.
2. A method according to claim 1, wherein the tab is provided with a tab hole.
3. A method according to claim 2, further comprising: providing a K-wire, and
    wherein the reorienting includes inserting the K-wire into the tab hole and using the K-wire to apply a bending load to the tab.
4. A method according to claim 3, wherein:
    the tab hole is sized to closely receive the K-wire in a fixed angle orientation.
5. A method according to claim 1, wherein:
    the reorienting is effected in situ.
6. A method according to claim 2, further comprising: providing a suture needle with attached suture, and
    inserting the suture needle completely through the tab hole to draw the suture through the tab.
7. A method according to claim 2, wherein:
    the reorientable tab of the provided plate includes a first tab at the first side of the plate and a second tab located intermediate between the first side and the second side of the plate, each of the first and second tabs including a respective non-threaded hole and each of the first and second tabs extend over the rim of the metaphyseal portion.
8. A method of stabilizing a fracture of a bone, the bone having a diaphyseal portion and a metaphyseal portion and having a concave articular surface at the end of the metaphyseal portion and a rim extending at least partially about the articular surface, the method comprising:
    a) providing a bone plate having a bone contacting surface, an opposite surface, a shaft portion defining a longitudinal axis and including a plurality of fastener holes to secure the shaft portion relative to the diaphyseal portion of the bone, and a head portion angled relative to the shaft portion to secure the head portion relative to the metaphyseal portion of the bone, the head portion having a first side and an opposing second side and a plurality of fastener holes provided therein adapted to receive fasteners therethrough, the second side of the head portion provided with a reorientable tab unitary with the head portion which extends longitudinally beyond the first side of the plate, the tab defining a non-threaded hole adapted to receive a suture needle;
    b) positioning the plate on the bone such that first side of the head portion seats proximally below the rim of the metaphyseal portion, and the tab extends over the rim of the metaphyseal portion;
    c) providing a curved suture needle with a suture attached thereto; and
    d) passing the curved suture needle through the hole and between the lower surface of the plate and the rim of the metaphyseal portion of the bone and through tissue.
9. A method according to claim 8, further comprising: reorienting the tab before the curved suture needle is passed through the hole in the tab.
10. A method according to claim 9, further comprising: providing a K-wire, and
    wherein the reorienting includes inserting the K-wire into the hole in the tab and using the K-wire to apply a bending load the tab.
11. A method according to claim 10, wherein:
    the hole in the tab is sized to closely receive the K-wire in a fixed angle orientation.
12. A method according to claim 9, wherein:
    the reorienting is effected in situ.
13. A method according to claim 8, wherein:
    the reorientable tab of the provided plate includes a first tab at the first side of the plate and a second tab located intermediate between the first side and the second side of the plate, each of the first and second tabs including a respective non-threaded hole and each of the first and second tabs extend over the rim of the metaphyseal portion.
14. A method of stabilizing a distal radius bone, the radius bone having a diaphysis and a metaphysis and defining a volar side, the metaphysis defining a boney crest inflexion point at the volar side and a distal articular surface having a volar rim, the method comprising:
    a) providing a bone plate having a bone contacting lower surface, an opposite upper surface, a shaft portion including a plurality of fastener holes to secure the shaft relative to the diaphysis of the radius bone, and a head portion angled relative to the shaft portion to secure the head portion relative to the volar side of the metaphysis of the radius bone, the head portion having a radial side and an ulnar side, the ulnar side having first and second spaced apart tabs distally extending beyond a distal edge of the radial side;
    b) positioning the plate on the volar side of the radius bone such that the radial side of the head portion seats proximally below the inflexion point, and each of the first and second tabs seats on the radius bone distally of the inflexion point and over the volar rim; and c) reorienting one or both of the first and second tabs to contour to the volar rim.

15. A method according to claim 14, wherein each of the first and second tabs is provided with a tab hole.

16. A method according to claim 15, further comprising:
providing a K-wire, and
wherein the reorienting includes inserting the K-wire into the tab hole of each of the first and second tabs and using the K-wire to apply a bending load to each of the first and second tab.

17. A method according to claim 16, wherein:
the tab hole of each of the first and second tabs is sized to closely receive the K-wire in a fixed angle orientation.

18. A method according to claim 14, wherein:
the reorienting is effected in situ.

19. A method according to claim 15, further comprising:

providing a suture needle with attached suture, and passing the suture needle completely through the tab hole of each of the first and second tabs to draw the suture through each of the first and second tabs.

20. A method according to claim 14, wherein:

the first tab is located at the ulnar side of the plate and the second tab is located at an intermediate medial-lateral location between the ulnar and radial sides of the plate, each of the first and second tabs extending distally of the inflexion point, and being adapted for reorientation toward the volar rim by a tool by inclusion of a non-threaded hole and a recess in the lower surface of the bone plate extending transversely between the head portion and the respective tabs.

* * * * *

UNITED STATES PATENT AND TRADEMARK OFFICE
CERTIFICATE OF CORRECTION

PATENT NO. : 9,510,881 B2
APPLICATION NO. : 14/291113
DATED : December 6, 2016
INVENTOR(S) : Castaneda et al.

It is certified that error appears in the above-identified patent and that said Letters Patent is hereby corrected as shown below:

In the Claims

In Column 9, Line 13, in Claim 16, delete "tab." and insert --tabs.--, therefor

Signed and Sealed this
First Day of May, 2018

Andrei Iancu
*Director of the United States Patent and Trademark Office*